United States Patent
Chamier et al.

(10) Patent No.: US 6,319,285 B1
(45) Date of Patent: Nov. 20, 2001

(54) CERAMIC ACETABULAR CUP WITH METAL COATING

(75) Inventors: Wilfried Von Chamier, Stuttgart; Kartmut Kalberer, Hochdorf; Hans-Georg Pfaff, Ostfildern, all of (DE)

(73) Assignee: Ceramtec AG Innovative Ceramic Engineering, Plochingen (DE)

( * ) Notice: Subject to any disclaimer, the term of this patent is extended or adjusted under 35 U.S.C. 154(b) by 0 days.

(21) Appl. No.: 09/581,427

(22) PCT Filed: Dec. 12, 1998

(86) PCT No.: PCT/EP98/08110
§ 371 Date: Sep. 28, 2000
§ 102(e) Date: Sep. 28, 2000

(87) PCT Pub. No.: WO99/30634
PCT Pub. Date: Jun. 24, 1999

(30) Foreign Application Priority Data

Mar. 13, 1997 (DE) .............................. 197 55 536

(51) Int. Cl.[7] ....................................... A61F 2/32
(52) U.S. Cl. ...................................... 623/22.32; 623/22.21
(58) Field of Search .............................. 623/22.11–22.46; 427/2.24, 456

(56) References Cited

U.S. PATENT DOCUMENTS

| | | | |
|---|---|---|---|
| 5,222,984 | * 6/1993 | Forte | 623/22 |
| 5,338,771 | * 8/1994 | Neumann et al. | 523/113 |
| 5,549,700 | * 8/1996 | Graham et al. | 623/22 |
| 5,571,193 | * 11/1996 | Kampner | 623/18 |
| 5,879,404 | * 3/1999 | Bateman et al. | 623/22 |
| 6,066,176 | * 5/2000 | Oshida | 623/22 |

* cited by examiner

Primary Examiner—Corrine McDermott
Assistant Examiner—Hieu Phan
(74) Attorney, Agent, or Firm—Antonelli, Terry, Stout & Kraus, LLP

(57) ABSTRACT

A hip-joint socket of a hip-joint endoprosthesis is provided, in which the bearing shell of the socket that mounts the ball head of the shaft is made of a ceramic material. The bearing shell (2) of the hip-joint socket (1; 11), in the region of its surface (4) with which it is inserted into the hip bone, is covered with a coating (5; 15) that is made of a biocompatible metal or a biocompatible metal alloy.

12 Claims, 2 Drawing Sheets

CERAMIC ACETABULAR CUP WITH METAL COATING

BACKGROUND OF THE INVENTION

The invention relates to a hip-joint socket of a hip-joint endoprosthesis in accordance with the preamble of the first claim.

Hip-joint endoprostheses as a rule are build up in a modular fashion. They consist, for example, of a shaft which is inserted into the femur. Plugged onto the shaft is a ball head which is mounted in a socket that is constructed from two parts. The socket consists of a socket housing, the so-called metal back, and a socket insert, the so-called insert. Furthermore, there are also systems which permit even more possibilities of combination and variation, for example in order to lengthen the shaft. With the modularly built up endoprostheses, implant components of different materials and sizes are connected together. For example, ball heads made of cobalt chromium are plugged onto a shaft of titanium alloy, or a socket insert of polyethylene or a ceramic material is inserted into a socket housing, as known, for example, from DE 196 112 48 A1. The combination of the individual parts is, as a rule, predetermined by the dimensions of the joint.

As known from the publication "Frettingkorrosion, ein Problem bei Hüftendoprothesen" by G. Willmann, Praktische Orthopädie, Rheumatologie-Endoprothetik, Volume 27, 1997, the disadvantage of the modular construction of endoprostheses is that, after having been assembled, instances of loosening can occur as a result of strains in the body that result in the relative movement between the individual parts of the prostheses and thus give rise to wear. In addition, on account of the plurality of possible components and possibilities for the assembly thereof, there is also a risk of confusion with regard to the sizes or a combination of prosthesis components that is not as prescribed. This can result in defective functioning of the prosthesis and thus ultimately in failure.

SUMMARY OF THE INVENTION

The object of the present invention is to put forward a hip-joint socket of a hip-joint endoprosthesis in which not only is incorrect assembly of the socket insert and socket housing precluded, but loosening of the two components caused by strain is also prevented.

The object is achieved with the aid of the characterising features of the first claim. Advantageous developments of the invention are claimed in the subclaims.

The invention gives rise to a one-piece hip-joint socket as an implant. As a result of coating the ceramic material of the socket with a biocompatible metal or a biocompatible metal alloy in the region in which the socket is inserted into the hip bone, a non-detachable connection results between the part of the prosthesis that functions as an insert in accordance with the prior art for the purpose of mounting the ball head and the so-called socket housing, this establishing the connection between the bone and the bearing shell for the ball head. Only one part is thus made available to the surgeon for the implantation of a socket, with the coating being matched in an optimum manner to the size and assembly of the ceramic bearing shell. The risk of incorrect assembly of the socket insert and socket housing is precluded. Furthermore, the risk that the connection between the insert and the housing will loosen on account of the strains in the prosthesis joint and that the prosthesis will wear as a result of the relative movement of the two components in relation to each other is precluded.

In an advantageous development of the invention, the surface of the bearing shell of the hip-joint socket that is to be coated is roughened. As a result, an intimate and solid mechanical connection of the coating with the ceramic body is guaranteed, since the coating neither reacts with the ceramic material chemically nor does it react therewith metallurgically. The surface of the ceramic body can be roughened, for example, by blasting with particles of hard material, by rough-grinding or etching.

In particular, two known and tested methods are available for the application of the coating. According to the first method, the coating is vapour-deposited thereon. The vapour-deposition can be effected, for example, by sputtering. In this connection, the metal that is to be applied is pulverized under high vacuum and is precipitated from the vapour phase onto the surface of the substrate. It is possible to produce a coating that is of the required layer thickness by means of repeated vapour-deposition.

The coating can also be sprayed thereon. Plasma-spraying is suitable for spraying on metals or metal alloys, in particular high-melting metals or metal alloys of titanium.

Plasma-spraying also presents the possibility of producing a coating to the required thickness. When a coating is of sufficient thickness, it is possible to roughen the surface of the coating. The roughness can be brought about by means of the method of application or by means of appropriate finishing in such a way that the bone tissue is offered the possibility of growing together with the surface and thus effecting reliable anchorage of the implant in the bone. The surface quality can already be achieved by means of the spraying technique, in particular in the case of plasma-spraying, so that no finishing is required.

Particularly good anchorage of the implant in the bone tissue is achieved if the coating is porous. In this case, the bone tissue can grow into the pores and thus provide the implant with a particularly good hold.

The thickness of the coating must be selected so that, on the one hand, it presents the bone tissue with a sufficiently large working surface to grow together therewith, but not so that, on the other hand, it is subject to the risk of fracture, something which can be the case, for example, with a porous coating that is too thick. A layer thickness which is thinner than 1 mm has therefore proved to be advantageous. A layer thickness of 50 micrometers to 150 micrometers, on the one hand, presents a sufficient level of thickness in order to form a structure that is favourable for ingrowth of the bone tissue and, on the other hand, presents sufficient stability of the coating per se.

All biocompatible metals and metal alloys are suitable for coating purposes. On account of their thermal and mechanical properties, titanium-based alloys, for example TiAl6V4 and TiAl6Nb7, have proved to be particularly advantageous.

All ceramic materials that have been applied successfully in prosthetics can be used as ceramic materials for the bearing shell of the hip-joint socket. Aluminium oxide with an appropriate level of purity has proved to be particularly advantageous for reasons of wear resistance, mechanical stability and medical compatibility.

In order to facilitate and accelerate the ingrowth of the implant into the bone, the coating can be provided with a bioactive covering. A covering that is known for these purposes is, for example, hydroxyapatite. The coating is applied in the same way and to the same level of thickness, as, for example, in the case of the coating of the shafts which are inserted into the femur.

DESCRIPTION OF THE DRAWINGS

The invention is explained in greater detail with reference to exemplifying embodiments. In the drawings.

DESCRIPTION OF THE PREFERRED EMBODIMENTS

Figure 1:
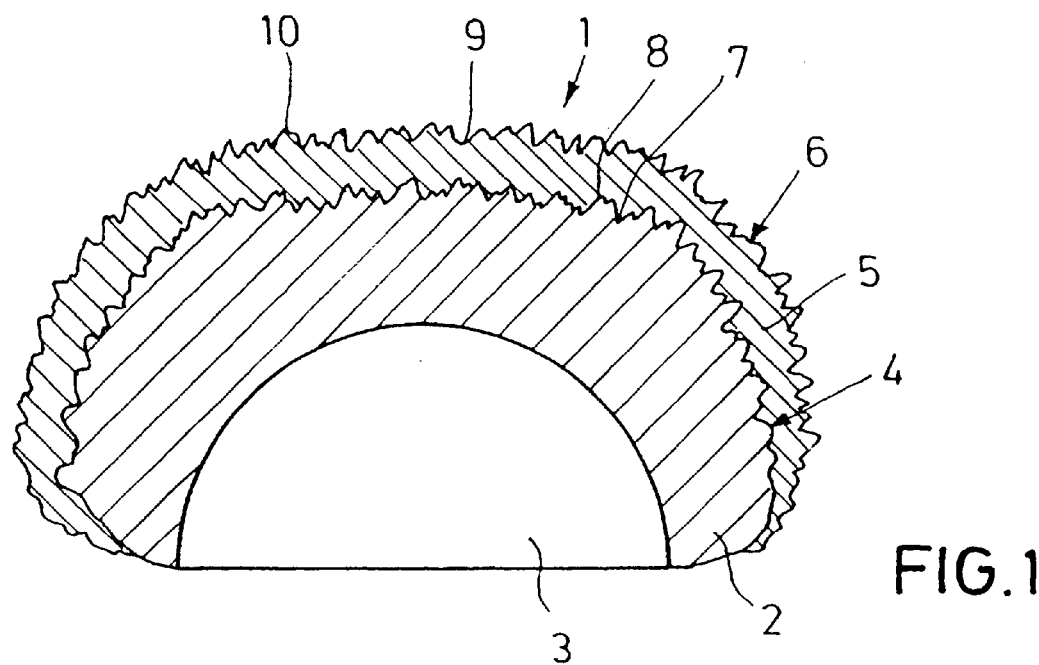
FIG. 1 shows a section through a hip-joint socket in accordance with the invention having a dense coating, the surface of which is roughened.

In FIG. 1 a hip-joint socket of a hip-joint endoprosthesis is denoted overall by 1. The hip-joint socket 1 is shown in section. The ceramic bearing shell 2 has a semi-spherical recess 3 to receive the ball head. The surface 4 of the ceramic body 2 that faces the hip bone is rough. The coating 5 clings, as if with claws, to this rough surface 4. Since the metal or the metal alloy does not enter into metallurgical or chemical combination with the ceramic material, good mechanical anchorage of the coating 5 is required. The coating 5 is therefore applied in such a way that, as far as possible, it fills in all the valleys 7 of the surface 4 of the bearing shell 2 and envelops all the peaks 8. In the present exemplifying embodiment, the coating of metal or a metal alloy is dense. Such a dense surface can be achieved, for example, by means of plasma-spraying with appropriately predetermined parameters, the flame temperature and the distance of the spraying device, or for example by vapour-deposition of a plurality of layers under a vacuum.

The coating 5 also has a rough surface G. The rough surface is to effect good anchorage of the implant in the bone by the bone substance filling in all the valleys 7 and growing around the peaks 8. The ingrowth into the bone substance can be accelerated in that the coating is provided with a bioactive covering, not shown here, as applied, for example, to shafts of hip-joint endoprostheses.

Figure 2:
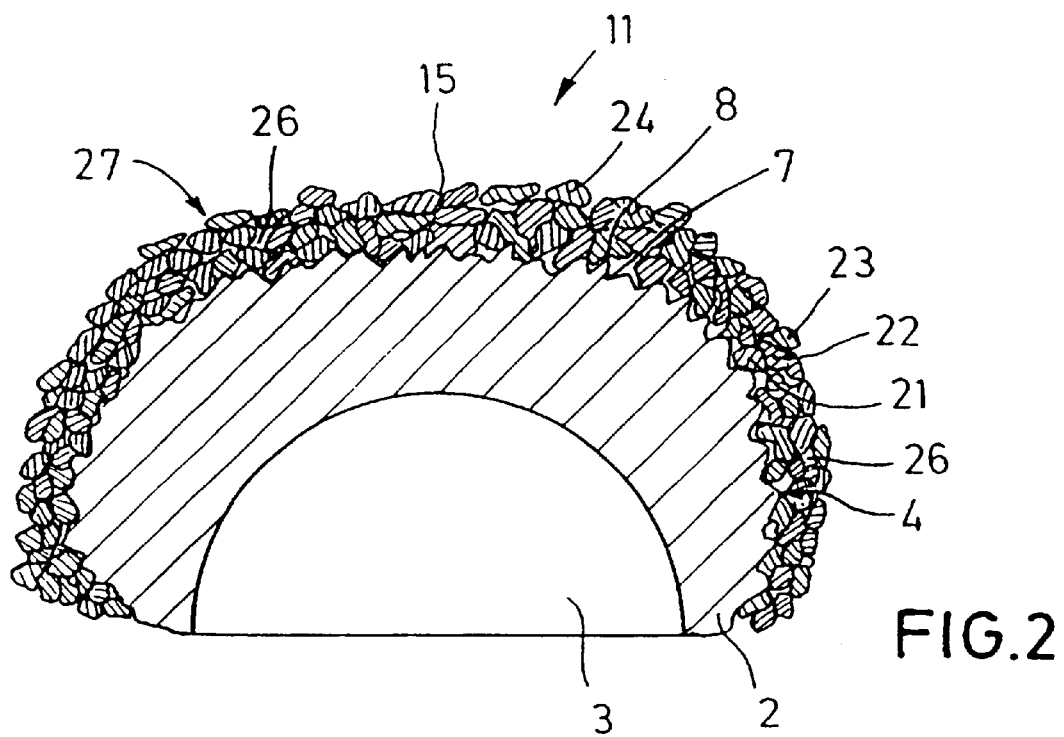
FIG. 2 shows a section through a hip-joint socket in accordance with the invention, the coating of which is porous.

FIG. 2 shows a further exemplifying embodiment of a hip-joint socket 11 in accordance with the invention. The section through the hip-joint socket 11 shows a comparable ceramic bearing shell 2 with the same recess 3 for the ball head and with a comparable rough surface 4. The coating 15 differs, however, in terms of structure, from the coating of the hip-joint socket of the previous exemplifying embodiment. The coating 15 is porous. A porous coating can be produced in particular by plasma-spraying a metal or a metal alloy. In the present exemplifying embodiment, a titanium alloy TiAl6V4 is sprayed onto a ceramic bearing shell 2 of aluminium oxide. The coating 15, in the present exemplifying embodiment, consists of three layers 21, 22 and 23 that are sprayed one on top of the other. By adjusting the temperature of the plasma flame and also the distance of the spraying device from the surface of the socket, it is possible to produce the structure of the coating 15 in question here. The droplets 24 of the metal alloy strike the surface 4 of the ceramic bearing shell 2. On account of the liquid or pasty state of the metal droplets, the valleys 7 of the surface 4 are filled in and the peaks 8 are surrounded. Owing to the fact that the metal or the metal alloy does not react with the ceramic material, when the droplets 24 cool the coating 15 is mechanically clamped together with the surface 4 of the ceramic bearing shell 2.

Figure 3:
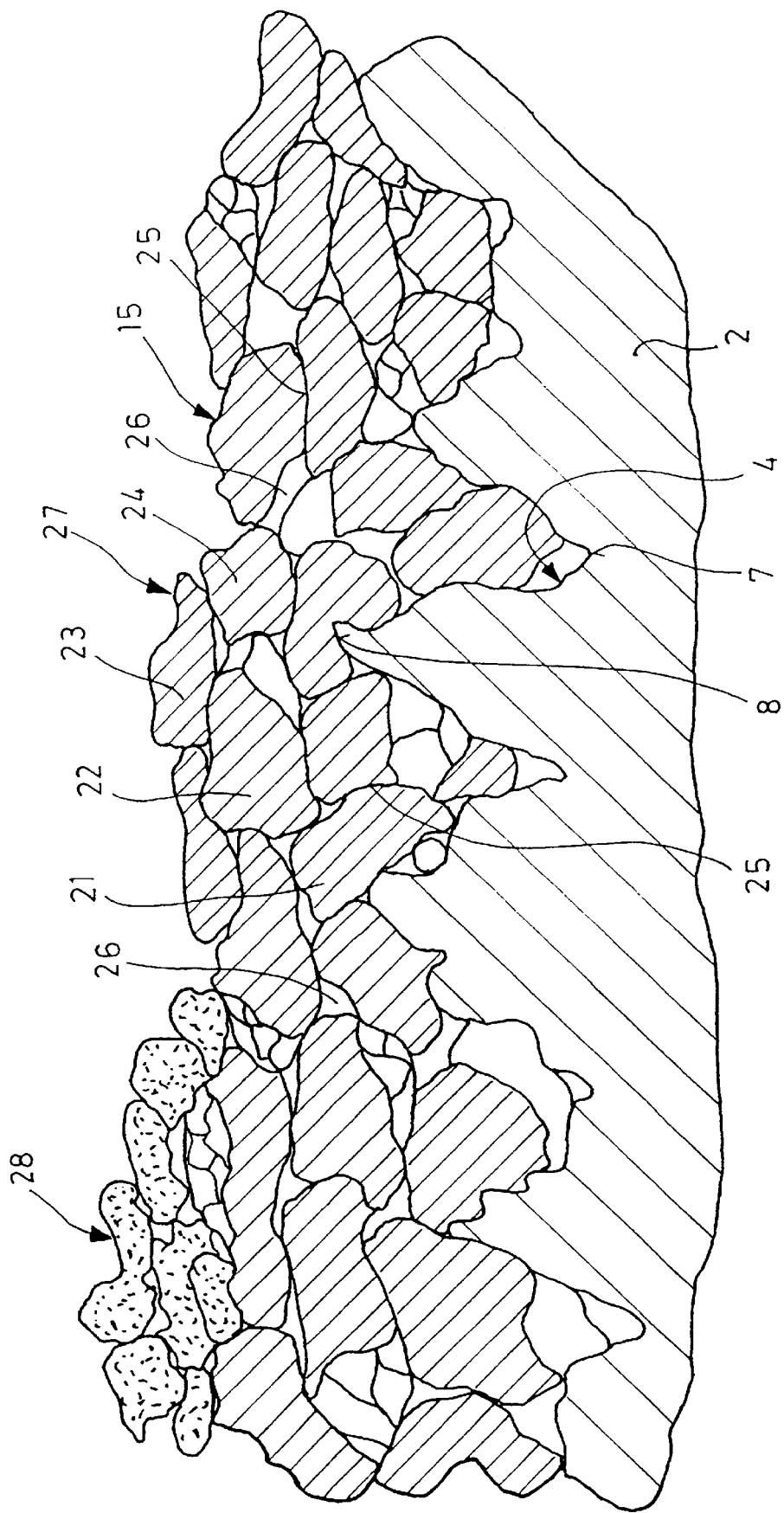
FIG. 3 shows an enlarged view of the section through the coating of the hip-joint socket in accordance with FIG. 2.

The porosity of the coating 15 is achieved by means of appropriate adjustment of the plasma-spraying method. Upon impact, the droplets do not form a dense layer, but are laid one on top of the other and side by side, fusing or welding together at the contact surfaces 25 (FIG. 3). If a droplet that is already located on the surface 4 is struck by another fresh droplet, on account of the thermal energy of the fresh droplet that is entrained therewith the surface of the first droplet can be re-fused thereon at the point of impact and an appropriate connection between the two droplets can develop at the contact surface. If, as in the present exemplifying embodiment, the coating 15 is sprayed thereon in a plurality of layers 21, 22 and 23, a porous layer, a coral structure, develops as a result of the connection of the droplets one with the other as has been described, with there remaining between the individual droplets 24 pores or cavities 26 into which the bone tissue can grow. As a result, good anchorage in the bone tissue of the coating 15, and thus of the hip-joint socket 1 as a whole, is achieved. In a manner that is not shown here, the ingrowing behaviour of the bone can be promoted further by the application of a bioactive layer, for example hydroxyapatite.

FIG. 3 shows an enlarged cutaway portion of the coating 15 of the hip-joint socket 11. The individual droplets 24 can be seen clearly, partly or completely in section. The droplets 24 of the first layer 21 have been mechanically connected to the valleys 7 and the peaks 8 of the rough surface of the ceramic material of the bearing shell 2. The second layer 22 and the third layer 23 of the coating 15 have not only been clamped together mechanically, but, at the contact surfaces 25 of the droplets 24, the droplets are also connected together metallurgically by fusion, baking or welding. The irregular structure of the droplets 24 that develops, in particular as a result of the droplets bursting open upon impact, likewise results in pores and cavities 26. In addition to these pores and cavities, a good possibility for ingrowth and anchorage is also presented to the bone tissue on the surface 27 of the coating 15 which, as a whole, is rough.

In FIG. 3 a portion of the coating 15 is additionally coated with a bioactive covering. These bioactive coverings, for example of hydroxyapatite, are known and as a rule are applied by spraying so that here, as well, a surface structure is formed that promotes the ingrowth of the bone tissue.

What is claimed is:

1. Hip-joint socket of a hip-joint endoprosthesis, in which the bearing shell of the socket that mounts the ball head of the shaft consists of a ceramic material, wherein the bearing shell (2) of the hip-joint socket (1; 11) in the region of its surface (4), with which it is inserted into the hip bone, is covered with a coating (5; 15) that is made of a biocompatible metal or a biocompatible metal alloy.

2. The hip-joint socket according to claim 1, wherein the surface (4) of the bearing shell (2) of the hip-joint socket (1; 11) that is to be coated is roughened in order to improve the hold of the coating (5; 15).

3. The hip-joint socket according to claim 1, wherein the coating (5) is vapour-deposited thereon.

4. The hip-joint socket according to claim 1 wherein the coating (15) is sprayed thereon.

5. The hip-joint socket according to claim 1, wherein the coating (15) consists of a plurality of layers (21, 22, 23).

6. The hip-joint socket according to claim 1, wherein the surface (6; 27) of the coating (5; 15) is rough.

7. The hip-joint socket according to claim 1, wherein the coating (15) is porous.

8. The hip-joint socket according to claim 1, wherein the thickness of the coating (5; 15) is thinner than 1 mm.

9. The hip-joint socket according to claim 8, wherein the thickness of the coating (5; 15) lies between 50 micrometers and 150 micrometers.

10. The hip-joint socket according to claim 1, wherein the coating (5; 15) consists of a titanium alloy.

11. The hip-joint socket according to claim 1, wherein the coating (5; 15) is provided with a bioactive covering (28).

12. The hip-joint socket according to claim 1, wherein the bearing shell (2) of the hip-joint socket (1) consists of aluminum oxide.

* * * * *